（12）United States Patent  
Subbotin

(10) Patent No.: US 10,640,787 B2  
(45) Date of Patent: May 5, 2020

(54) PROCESS FOR MIXING NUCLEIC ACIDS WITH TRANSFECTION REAGENTS FOR DELIVERY

(71) Applicant: Vladimir M Subbotin, Madison, WI (US)

(72) Inventor: Vladimir M Subbotin, Madison, WI (US)

(\*) Notice: Subject to any disclaimer, the term of this patent is extended or adjusted under 35 U.S.C. 154(b) by 353 days.

(21) Appl. No.: 15/661,717

(22) Filed: Jul. 27, 2017

(65) Prior Publication Data

US 2019/0032085 A1    Jan. 31, 2019

(51) Int. Cl.
*C12N 15/87* (2006.01)
*A61K 31/7105* (2006.01)
*A61K 48/00* (2006.01)
*C12N 15/88* (2006.01)
*C12N 15/11* (2006.01)

(52) U.S. Cl.
CPC .......... *C12N 15/87* (2013.01); *A61K 31/7105* (2013.01); *A61K 48/0008* (2013.01); *C12N 15/88* (2013.01); *C12N 15/111* (2013.01); *C12N 2310/14* (2013.01); *C12N 2310/3517* (2013.01); *C12N 2320/32* (2013.01)

(58) Field of Classification Search
None
See application file for complete search history.

(56) References Cited

PUBLICATIONS

Belliveau, et al. (2012) "Microfluidic Synthesis of Highly Potent Limit-size Lipid Nanoparticles for In Vivo Delivery of siRNA", Molecular Therapy-Nucleic Acids, 1: e37, 9 pages. (Year: 2012).*

\* cited by examiner

*Primary Examiner* — Robert M Kelly
(74) *Attorney, Agent, or Firm* — Mark K Johnson

(57) ABSTRACT

A process is described for transfecting nucleic acids into cells in vivo by mixing transfection reagents and the nucleic acids immediately prior to injection. The process comprises introducing the transfection reagents and the nucleic acids into a mixing chamber by a first portal for introducing the transfection reagents, a second portal for introducing the nucleic acids where the transfection reagents and nucleic acids are mixed together to form particles and pushing the particles through an injection portal into a mammal in less than 1 second after introduction thereby transfecting cells in the mammal.

15 Claims, 12 Drawing Sheets
(12 of 12 Drawing Sheet(s) Filed in Color)

PROCESS FOR MIXING NUCLEIC ACIDS WITH TRANSFECTION REAGENTS FOR DELIVERY

FIELD OF THE INVENTION

Transfection reagents are combined and mixed in a micro chamber that receives both cationic lipids and nucleic acids through separate channels which are then directed into an injection needle less than one second after mixing, facilitating the delivery of cationic lipids/nucleic acids particles to targeted organs.

BACKGROUND

The present invention relates to cationic polymer-nucleic acid compounds which have use in the delivery of nucleic acid to cells in biological systems, for instance in in vitro cell transfection research as well as in vivo delivery. The invention also relates to methods of mixing such compounds and potentially to gene therapy using such compounds.

The control of living processes is mediated through nucleic acids. Nucleic acids encode proteins which, as enzymes, hormones and other regulatory factors, carry out the processes which enable living organisms to function. Nucleic acids also encode for regulatory sequences which control the expression of proteins.

Because of its central role in living organisms, nucleic acids make an ideal therapeutic target. It is thought that many diseases could be controlled by the manipulation of nucleic acids in living organisms.

The key factor limiting therapies based on nucleic acid manipulation is the ability to deliver nucleic acids to the cells. Nucleic acids are fragile molecules which are highly negatively charged (one negative charge per phosphate group) and which are readily cleaved by nucleases present both in extracellular fluids and intracellular compartments. As a highly charged molecule it will not cross the lipid membranes surrounding the cell, nor can it readily escape from endosomal compartments involved in the uptake of macromolecules into cells. Even RNAi molecules, although smaller in molecular weight, show significant problems of stability and uptake.

Cationic lipid formulations suffer from a number of shortcomings. Cationic lipid formulations are unstable and have a relatively short shelf life. The short shelf life is at least partly due to the tendency of these formulations to aggregate.

The discovery of altering gene expressions by delivery to mammalian cells of nucleic acids such as plasmid DNA, double stranded DNA and small interference RNA (siRNA) offers the potential ability to treat a variety of diseases. However, therapeutic applications of this technology have been slow to materialize. A first obstacle is the targeting of a particular organ or tissue. It was thought that attaching specific ligands which have affinity to receptors of targeted cells to nucleic acids would solve the problem. However the number of suitable ligand/receptor combinations is limited, e.g. application of galactose-derived ligands to target hepatocytes. Additionally, receptor-mediated nucleic acid entry into cells is inevitably associated with endosomal formation and nucleic acid degradation in lysosomes. To prevent lysosome formation and nucleic acid degradation endosomolytic agents are commonly used. However, attaching molecules that facilitate endosome disruption and nucleic acid release (e.g. melittin-like peptide) cause severe toxicity.

Another obstacle is the high levels of nucleases in all extracellular compartments, causing degradation of nucleic acids injected subcutaneously or intravenously. Attaching nuclease-protective groups to nucleic acid complexes makes targeting and cell entry more difficult, and significantly increases the cost of the technology.

Complexation of nucleic acids with cationic liposomes offers some protection from nucleases and can facilitate fusion of a small portion of liposomes with cells which avoids lysosome formation. However, liposomal nucleic acid delivery lacks organ-specific targeting and mostly targets macrophages, yet results in toxicological effects due to the cationic surface charge.

As it stands today, there is no simple technology allowing nucleic delivery to cells in vivo. All attempts to deliver nucleic acids, more specifically, siRNA to cancer cells in vivo to knock down inhibitory checkpoint proteins failed, as did all attempts to deliver siRNA though blood-brain barrier to brain neurons.

We have developed new simple technology that overcomes the stated obstacles and sufficiently delivers nucleic acids to cells in normal organs as well as to cancer cells in experimental tumor models—in vivo.

It is an object of the invention to overcome at least some of the above problems.

BRIEF DESCRIPTION OF THE DRAWINGS

The patent or application file contains at least one drawing executed in color, copies of this patent or patent application publication with color drawings will be provided by the Office upon request and payment of the necessary fee.

SUMMARY

Figure 1:
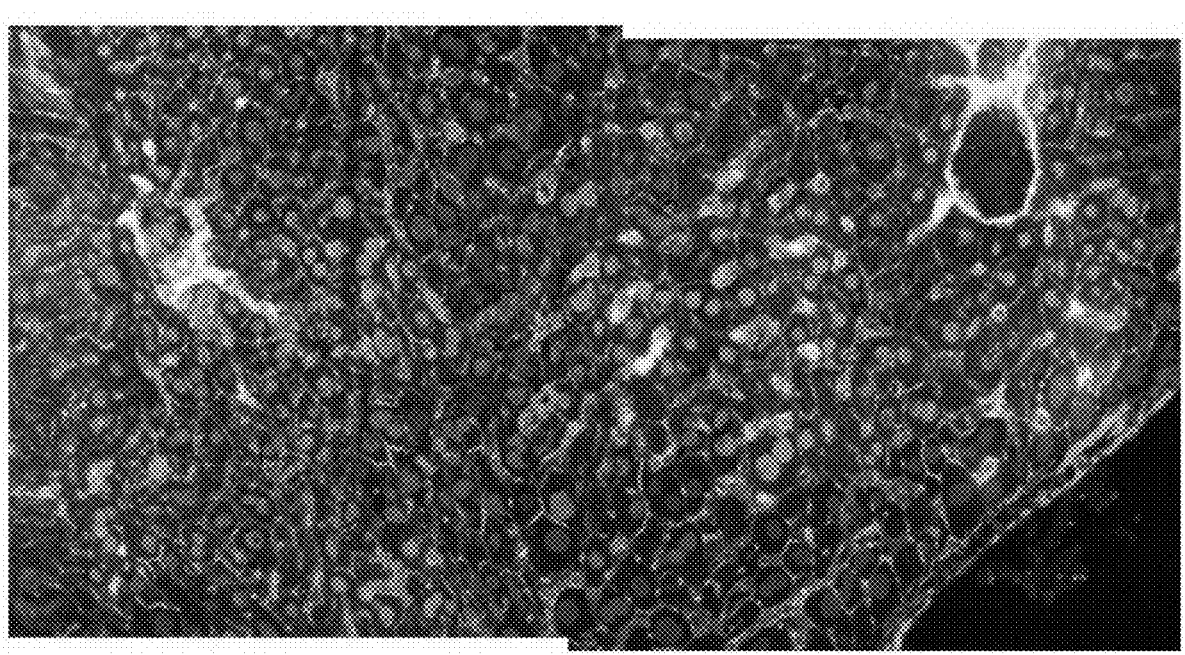
FIG. 1 shows Cy3-labeled siRNA delivery to cells of a mouse liver via the portal vein in two consecutive microscopic fields, 1 hour after injection using confocal microscopy, three channels. Green—actin stained with Alexa 488, blue nuclei stained with ToPro3, red—Cy3 signal. Magnification×400.

For more than three decades cationic lipids have been successfully used for in vitro delivery of nucleic acids to cells, and many have been commercialized. Although some studies reported in vivo nucleic acid delivery to animals, for example to vascular cells, to lung epithelium, to brain neurons, overall results of in vivo experiments were significantly less encouraging than in vitro results, and currently the in vivo approach is practically abandoned.

Giving tremendous effectiveness of in vitro transfection and insufficient transfection in in vivo experiments, it is obvious that all current protocols of cationic lipids/nucleic acid delivery resulted in formation of particles which are not effective for cells transfection in natural environment, i.e. in vivo.

All protocols require mixture of cationic lipids and nucleic acids in a tube by pipetting following by Vortex swirl/incubation at room temperature for at least 10-15 minutes prior to delivery. This is standard time of incubation for particles' characterization, particular for a size distribution, which characterized as 100-300 nm. This incubation time resulted in formation of a particle size which is not effective in in vivo conditions and shortening of incubation time by orders of magnitude could result in cationic lipids/nucleic acids particles with effective penetrable properties.

In a preferred embodiment, we mounted a mixing micro chamber that receives cationic lipids and nucleic acids separately using an injection needle, which facilitates delivery of cationic lipids/nucleic acids formulation to targeted organs in less than one second after mixing. The time of complexation is 100× to 1000× shorter than current protocols. Another benefit of our invention is that nucleic acids in our technology do not require protection groups.

In a preferred embodiment, using our mixing technique we have achieved significant nucleic acid delivery to cells of various organs in mice (hepatocytes, biliary epithelial cells, brain neurons) and experimental mouse cancer (mouse colon carcinoma, CT26, growing in liver and subcutaneously). Successful delivery to cells was evident from nuclear co-localization of Cy3-labeled siRNA and ToPro3 (nuclear) signals, because nucleic acids accumulated in nuclei after cytoplasmic delivery.

In a preferred embodiment, applicants describe a process for transfecting nucleic acids into cells in vivo by mixing transfection reagents and the nucleic acids immediately prior to injection. The process comprises introducing the transfection reagents and the nucleic acids into a mixing chamber by a first portal for introducing the transfection reagents. Then using a second portal for introducing the nucleic acids into the the mixing chamber where the transfection reagents and nucleic acids are mixed together to form particles. The particles are exiting through an injection portal into a mammal in less than 5 seconds after introduction thereby transfecting the mammalian cell. The cell is thereby transfected.

The process also comprises a third portal for introducing a solution for washing the mammalian organ. The third portal introduces the wash solution into the mammal prior to the particles being exiting through the injection portal.

In a preferred embodiment the transfection reagents contain cationic lipids. The nucleic acids may consist of DNA, RNA and RNAi. The cationic lipids combine with the nucleic acids to form a particle which is injected into the mammal and then the particle transfects a cell. The process of introducing the transfection reagents, introducing the nucleic acids, mixing and pushing the particles is continuous over a period of time determined by the volume of solution required.

EXAMPLES

All mouse surgeries were performed under Isoflurane anesthesia in semi-sterile conditions. Surgical approaches included abdominal wall incision and skin incision on the right side of a neck followed by application of retractors to open surgical fields. After nucleic acid delivery, surgical incisions were sutured and all mice recovered after anesthesia and were monitored for at least one hour. No visible signs of toxicity or complications were observed within this time.

In experiments with vascular/bile duct delivery, a needle was inserted into supplying vessels (hepatic and carotid arteries, or portal vein) or into the bile duct and secured with a micro clamp. In most experiments blood or bile from targeted organs was washed out by slow perfusion using 1 mL of isotonic glucose (10 mM Hepes and 5 mM NaCl) with aid of pump #3. After blood replacement by isotonic glucose, pumps #2 & 3 were simultaneously started. A volume of 20-60 µL of cationic lipid transfection reagent (TransIT-LT1 or TransIT-TKO) was injected into the mixing chamber by a first syringe pump (#1), while 5-20 µg Cy3-labeled siRNA in 200-600 µL of isotonic glucose was simultaneously injected into the mixing chamber by a second syringe pump (#2) using a time of injection of 30 seconds. For liver targeting, a needle was inserted into the portal vein and the hepatic artery was clamped. About thirty seconds after injection, a needle was retracted, and blood flow was restored. Bleeding was controlled by application of hemostatic Gelfoam sponge with a Q-tip. Surgical sites were sutured and all reported animals recovered from anesthesia and were sacrificed one hour after delivery.

Figure 12:
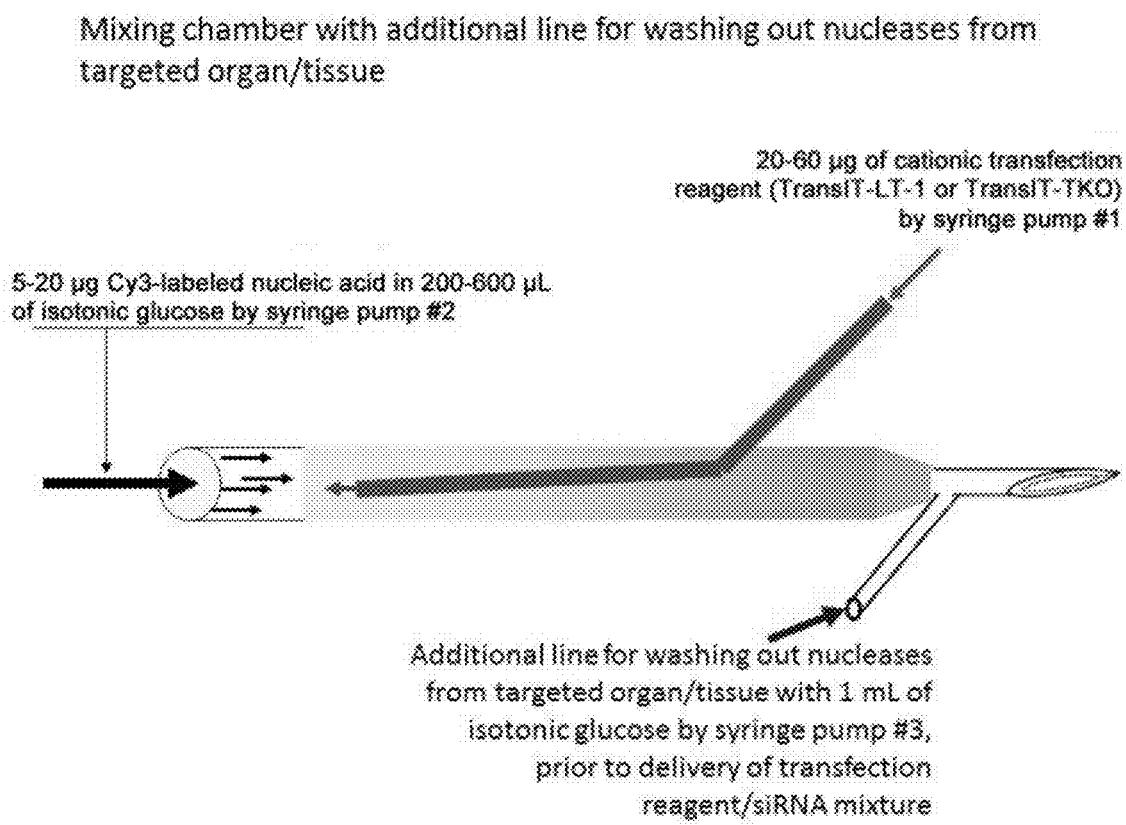
FIG. 12 shows a schematic of a preferred device for in vivo delivery of cationic lipids/nucleic acids particles with minimal incubation time (or less than 1 second).

A schematic of one preferred embodiment of the delivery mechanism is shown in FIG. 12. The schematic shows the three pump channels into the mixing chamber and one outlet into animal tissue which provides fast (less than 1 second) mixing of transfection reagents and nucleic acids immediately prior to injection. This is only one configuration of the many that could be configured based upon the description in this specification.

Example 1

Figure 2:
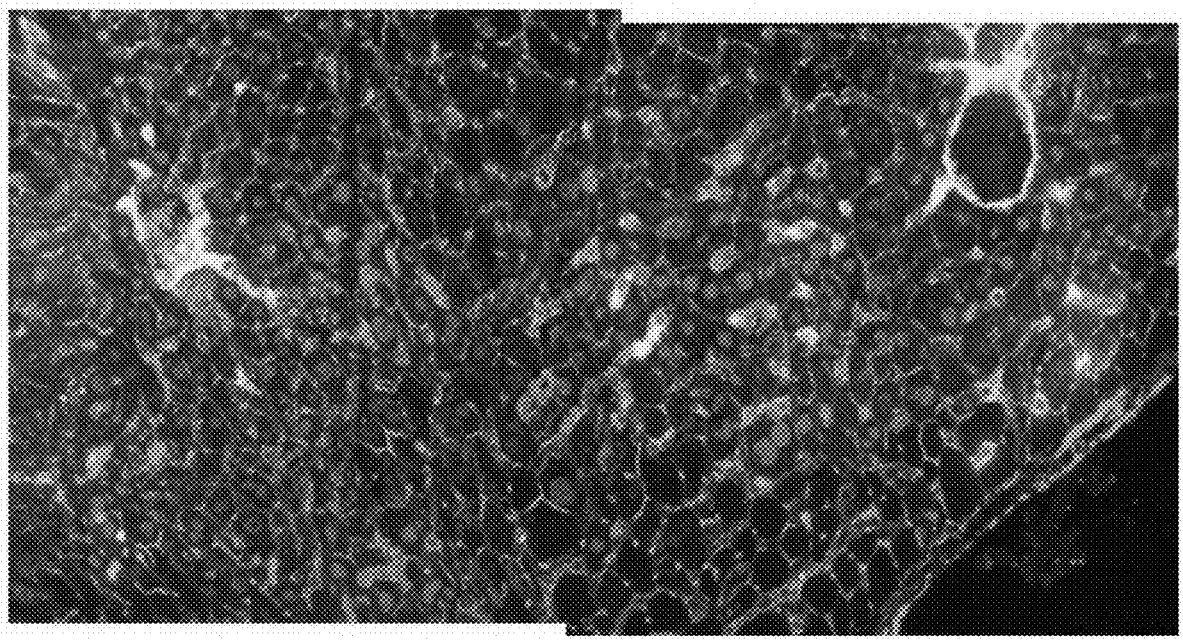
FIG. 2 shows FIG. 1 with blue channel (nuclear staining) turned off for better visualization of Cy3 signal.

Under isoflurane anesthesia a mouse abdomen was opened and the liver vasculature was visualized. The hepatic artery was clamped and a needle was inserted into the portal vein and secured with a micro clamp. The liver was pre-flushed with 1 ml of IG (FIG. 12). Then 20 µg of Cy3-labeled siRNA in 40 µl of isotonic glucose (10 mM Hepes and 5 mM NaCl) was injected into the mixing chamber simultaneously with 60 µl of TransIT-TKO in 340 µl of isotonic glucose, and the resulting mixture was continuously injected into the portal vein within 30 seconds. The mouse was sutured, recovered after anesthesia and sacrificed 1 hour later with no signs of toxicity. Liver specimens were snap-frozen in OCT on liquid nitrogen. Frozen sections were stained with Alexa-488 Falloidin and ToPror-3 and examined under confocal microscope. FIG. 1 demonstrates two consecutive fields and magnification 400×, were almost all nuclei of liver cells showed strong Cy3 signal. FIG. 1 shows nuclear accumulation of Cy3-labeled siRNA at 1 hour after delivery. In FIG. 2 with the blue channel (DNA staining with ToPro-3) turned off, shows that majority of cells in liver were targeted.

In all following experiments the ratio of transfection solution/siRNA/isotonic glucose was changed to 1:1:10, to decrease concentration of ethanol and to minimize possible cell injury. Pure transfection solution was delivered to the micro chamber by pump #1, while siRNA in isotonic glucose (10 mM Hepes and 5 mM NaCl) was injected into mixing chamber by pump #2.

Example 2

Figure 3:
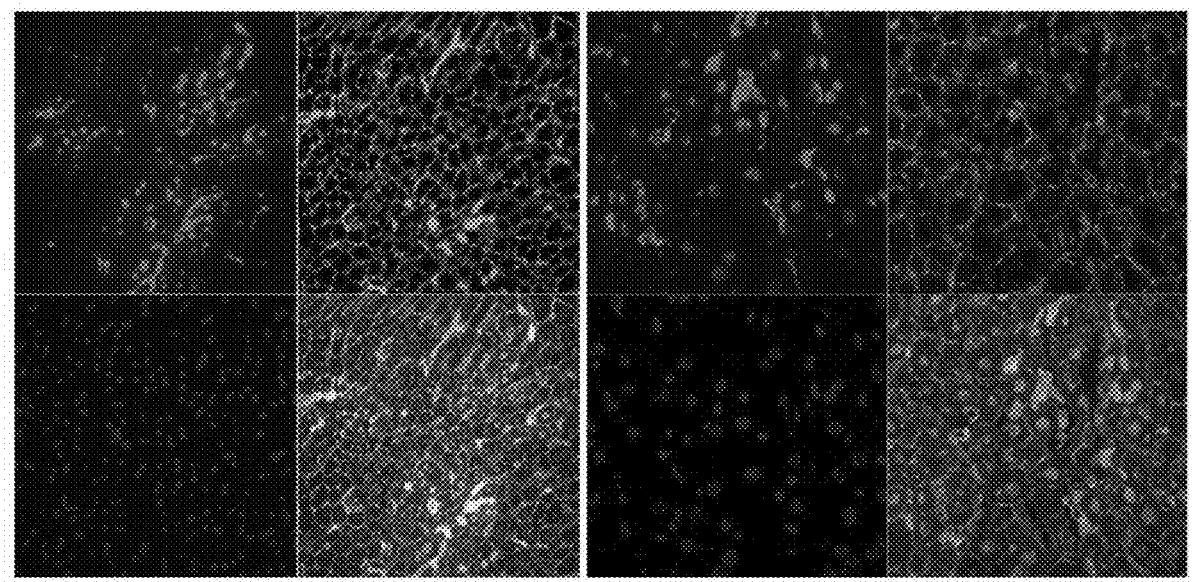
FIG. 3 shows Cy3-labeled siRNA delivery to cells of a mouse liver via portal vein in two microscopic fields, 1 hour after injection.

Surgery, liver pre-flushed with IG, specimen preparation, and microscopy were performed as described in Example #1. 60 µl of TransIT-TKO was injected into the mixing chamber by pump #1 simultaneously with 20 µg of Cy3-labeled siRNA in 600 µl of isotonic glucose by pump #2. FIG. 3 shows strong co-localization of Cy3 signal and nuclear staining. Left image—magnification 400×, right image—magnification 630×.

Figure 4:
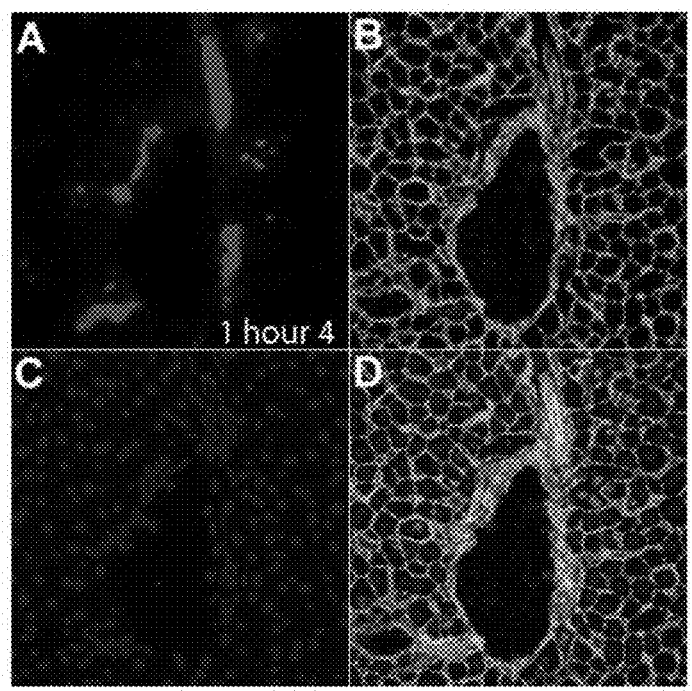
FIG. 4 shows Cy3-labeled siRNA delivery to bile duct epithelial cells (nuclei) of a mouse liver via the bile duct 1 hour after injection, magnification×400.
Figure 5:
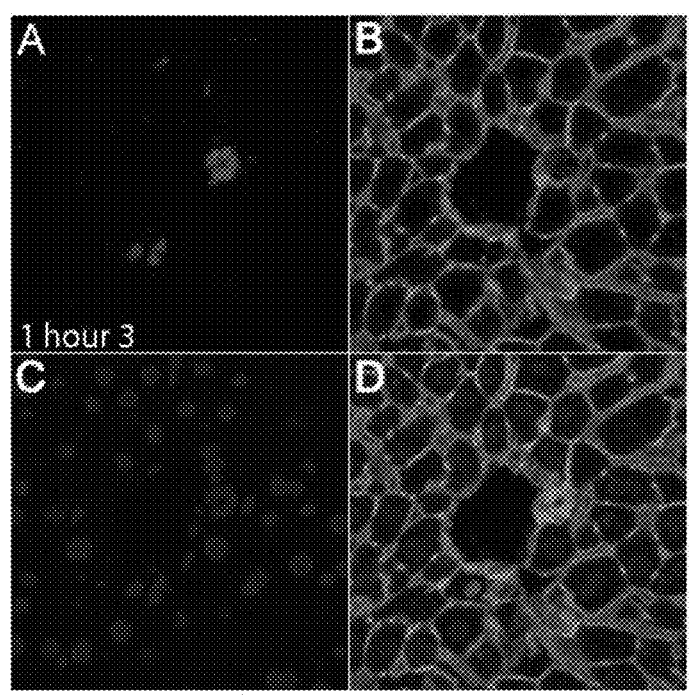
FIG. 5 shows Cy3-labeled siRNA delivery to bile duct epithelial cells of a mouse liver via the bile duct 1 hour after injection, magnification×630.

In experiments with siRNA delivery to bile duct epithelial cells surgery, specimen preparation and microscopy were performed as described in Example #1. For bile duct cannulation a hollow 30 gauge catheter shaft containing a non-traumatic tip was inserted into the bile duct through a small puncture of the duodenal wall and through the sphincter of Oddi. A fitted clamp was used together with the catheter to restrict the direction of fluid flow through the bile duct. Biliary was tree pre-flashed with 100 µl on isotonic glucose (pump #3). 10 µl of TransIT-LT-1 was injected into mixing chamber by pump #1 simultaneously with 10 µg of Cy3-labeled siRNA in 100 µl of isotonic glucose by pump #2. FIG. 4 shows strong Cy3 signal in bile ducts and few hepatocytes one hour after Cy3-labeled siRNA delivery, magnification 400×. FIG. 5 shows Cy3-labeled siRNA delivery to bile duct epithelial cells (nuclei), and as well Cy3 signal in three hepatocytes, magnification 630×.

Figure 6:
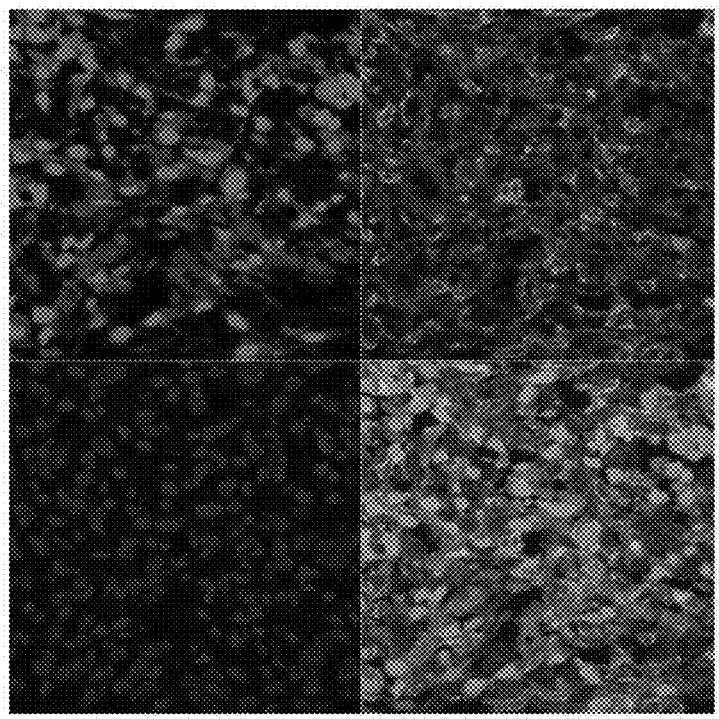
FIG. 6 shows Cy3-labeled siRNA delivery to cells of colonic carcinoma in a mouse liver via the hepatic artery, 1 hour after injection.
Figure 7:
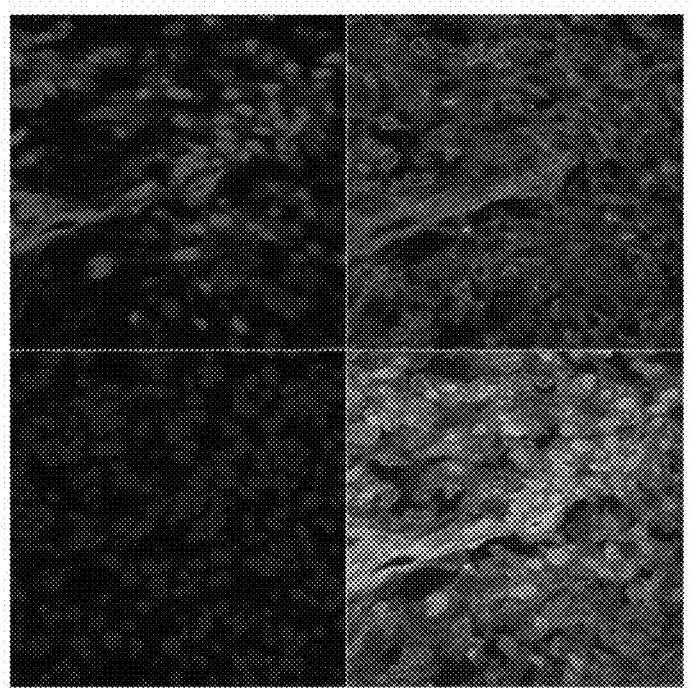
FIG. 7 shows Cy3-labeled siRNA delivery to cells of colonic carcinoma in a mouse liver via the hepatic artery, 1 hour after injection and showing Cy3-labeled siRNA also accumulated in tumor cells (nuclei) and in vasculature strictures.
Figure 8:
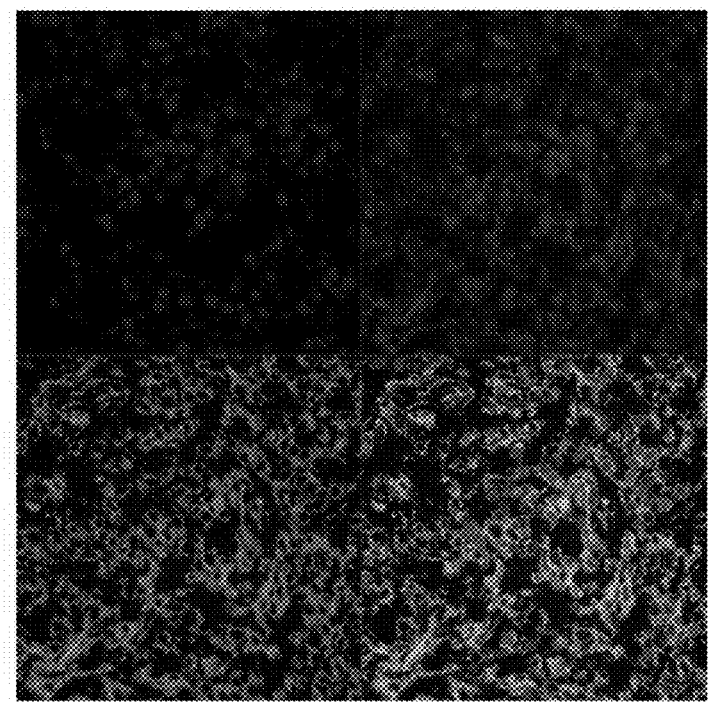
FIG. 8 shows Cy3-labeled siRNA delivery to cells of colonic carcinoma in a mouse liver via the hepatic artery, 1 hour after injection and showing Cy3-labeled siRNA accumulated in tumor cells (nuclei).
Figure 9:
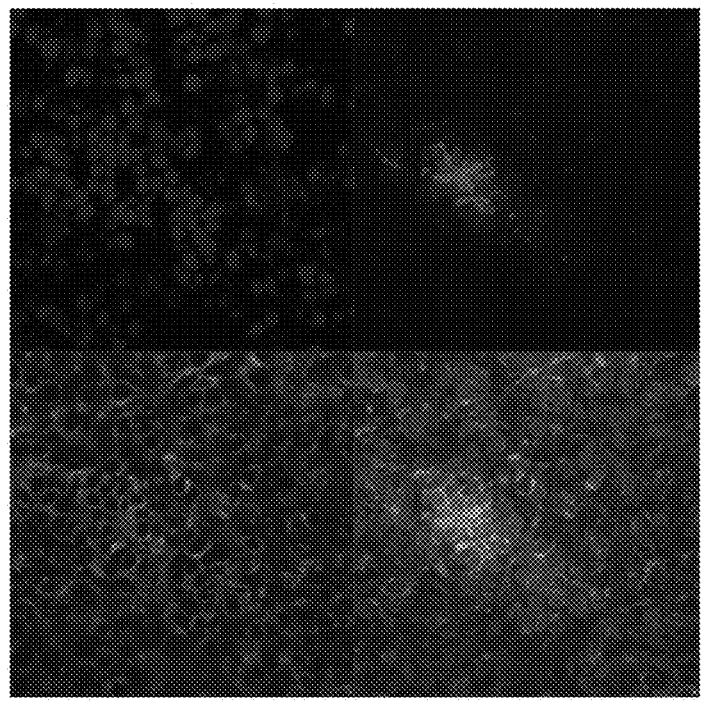
FIG. 9 shows Cy3-labeled siRNA delivery to cells of subcutaneous colonic carcinoma in via direct injection into the tumor, 1 hour after injection and showing Cy3-labeled siRNA accumulated in tumor cells (nuclei) and between cells.

Example 3 siRNA delivery to tumor cells. Liver tumors in BALB/c mice were induced by local liver injection of $10^5$ CT-26 mouse colon carcinoma cells in Matrigel or by subcutaneous injection. After 3 weeks, surgery, specimen preparation and microscopy were performed as described in Example #1. Hepatic artery access was performed via right gastro-duodenal artery as previously described. Liver tumors were pre-perfused with 200 µl of isotonic glucose by pump #3. 20 µl of TransIT-LT-1 was injected into mixing chamber by pump #1 simultaneously with 10 µg of Cy3-labeled siRNA in 200 µl of isotonic glucose by pump #2. FIG. 6 showed Cy3-labeled siRNA nuclear accumulation in majority cells in the middle of tumor (both cancer and stromal cells) magnification 630×. FIG. 7 shows Cy3-labeled siRNA accumulation in tumor cells (nuclei) and in vasculature strictures in tumor periphery, magnification 630×. The siRNA delivery was also performed with transfection reagent TransIT-TKO as described above. FIG. 8 shows Cy3-labeled siRNA delivery to cells of colonic carcinoma in mouse liver via hepatic artery, 1 hour after injection. Cy3-labeled siRNA accumulated in tumor cells (nuclei), both cancer and stromal cells, magnification 400×. FIG. 9 shows Cy3-labeled siRNA delivery to cells of subcutaneous colonic carcinoma in via direct injection into tumor, 1 hour after injection. Cy3-labeled siRNA accumulated in tumor cells (nuclei) and between cells.

Figure 10:
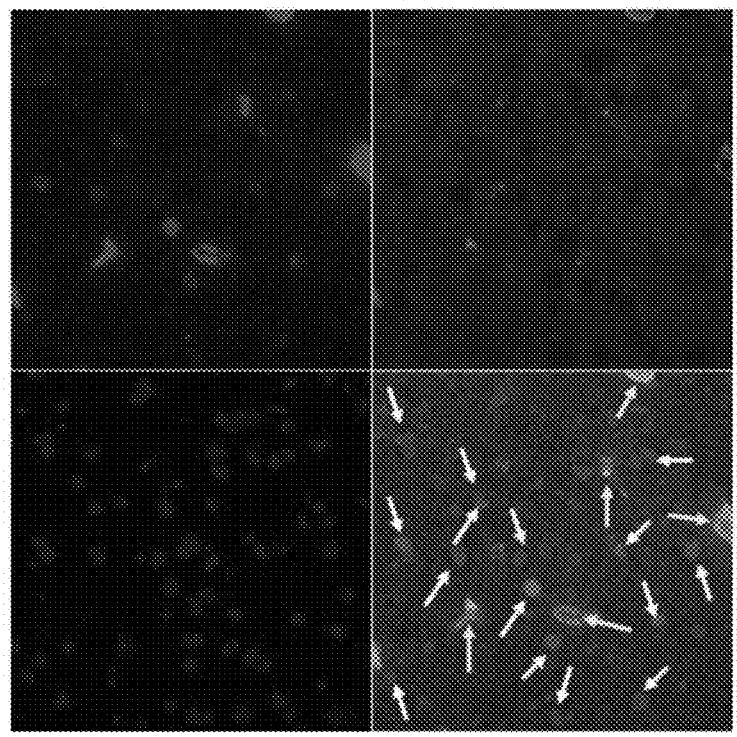
FIG. 10 shows Cy3-labeled siRNA delivery to neurons of a mouse frontal cerebral cortex via carotid artery injection, 1 hour after injection (white arrows), yellow arrows indicate Cy-3 signal in vasculature.
Figure 11:
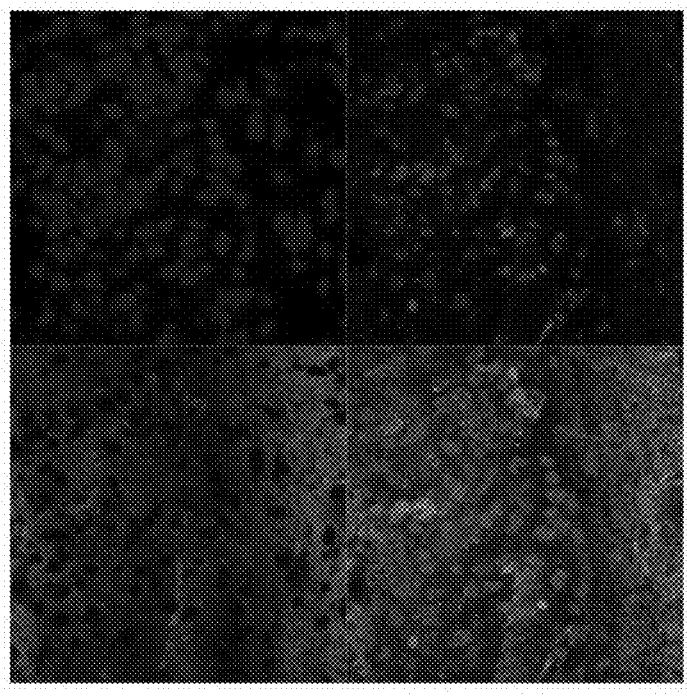
FIG. 11 shows Cy3-labeled siRNA delivery to neurons of a mouse frontal cerebral cortex via carotid artery injection, 1 hour after injection and showing Cy3-labeled siRNA accumulated in neurons (nuclei).

Example 3 siRNA delivery to brain cells. Under Isoflurane anesthesia, a skin incision was performed on the right side of a mouse neck. The right carotid artery was visualized, a needle was inserted into carotid artery and secured with micro clamp. The right brain hemisphere was perfused with 200 µl of isotonic glucose by pump #3. 20 µl of cationic lipid transfection reagent was injected into the mixing chamber by pump #1 simultaneously with 10 µg of Cy3-labeled siRNA in 200 µl of isotonic glucose by pump #2. FIG. 10 shows Cy3-labeled siRNA delivery to neurons of mouse frontal cerebral cortex using 20 µl of TransIT TKO transfection reagent. White arrows indicated Cy3-labeled neurons, yellow arrow indicated Cy-3 signal in vasculature. FIG. 11 shows Cy3-labeled siRNA delivery to neurons of mouse frontal cerebral cortex (pyramidal layer) using TransIT LT-1 transfection reagent, 1 hour after injection. Cy3-labeled siRNA accumulated in neurons (nuclei).

I claim:

1. A process for transfecting nucleic acids into cells in vivo by mixing transfection reagents and the nucleic acids immediately prior to injection, comprising: introducing the transfection reagents into a mixing chamber by a first portal, a second portal for introducing the nucleic acids into the mixing chamber, mixing the transfection reagents and nucleic acids together to form particles and then exiting the particles through an injection portal into a mammal in less than 5 seconds after introduction thereby transfecting the mammal.

2. The process of claim 1 wherein the particles are exiting through an injection portal into a mammal in less than 3 seconds after introduction.

3. The process of claim 2 wherein the particles are exiting through an injection portal into a mammal in less than 1 second after introduction.

4. The process of claim 1 wherein the particles are exiting through an injection portal into a mammalian organ.

5. The process of claim 4 wherein the particles are exiting through an injection portal and then transfected into a mammalian cell.

6. The process of claim 4 further comprising a third portal for introducing a solution for washing the mammalian organ.

7. The process of claim 1 wherein the transfection reagents contain cationic lipids.

8. The process of claim 1 wherein the nucleic acids consist of DNA.

9. The process of claim 1 wherein the nucleic acids consist of RNA.

10. The process of claim 9 wherein the nucleic acids consist of RNAi.

11. The process of claim 10 wherein the nucleic acids consist of siRNA.

12. The process of claim 1 wherein the particles contain cationic lipids and DNA.

13. The process of claim 12 wherein the particles contain cationic lipids and plasmid DNA.

14. The process of claim 1 wherein the particles contain cationic lipids and RNA.

15. The process of claim 14 wherein the particles contain cationic lipids and siRNA.

* * * * *